United States Patent
Sakai et al.

(10) Patent No.: US 8,664,157 B2
(45) Date of Patent: Mar. 4, 2014

(54) RECORDING MATERIAL USING PHENOL COMPOUND

(75) Inventors: Hiroshi Sakai, Ichihara (JP); Shuntaro Kinoshita, Ichihara (JP); Tadahiro Kondo, Ichihara (JP); Kazumi Jyujyo, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/816,318

(22) PCT Filed: Aug. 29, 2011

(86) PCT No.: PCT/JP2011/004782
§ 371 (c)(1),
(2), (4) Date: Feb. 11, 2013

(87) PCT Pub. No.: WO2012/029276
PCT Pub. Date: Mar. 8, 2012

(65) Prior Publication Data
US 2013/0137570 A1    May 30, 2013

(30) Foreign Application Priority Data
Sep. 1, 2010 (JP) .................................. 2010-195363

(51) Int. Cl.
*B41M 5/333* (2006.01)
*C07C 233/29* (2006.01)

(52) U.S. Cl.
USPC .................. 503/216; 106/31.18; 564/182

(58) Field of Classification Search
None
See application file for complete search history.

(56) References Cited

FOREIGN PATENT DOCUMENTS

| GB | 2 056 103 A | 3/1981 |
|---|---|---|
| JP | A-56-27132 | 3/1981 |
| JP | A-2-153789 | 6/1990 |
| JP | A-6-171225 | 6/1994 |
| JP | A-11-78247 | 3/1999 |
| JP | A-2003-305959 | 10/2003 |

OTHER PUBLICATIONS

International Preliminary Report on Patentability issued in International Patent Application No. PCT/JP2011/004782 issued Mar. 5, 2013.
International Search Report issued in International Patent Application No. PCT/JP2011/004782 mailed Sep. 20, 2011.

*Primary Examiner* — Bruce H Hess
(74) *Attorney, Agent, or Firm* — Oliff PLC

(57) ABSTRACT

An object of the present invention is to provide a recording material or a recording sheet that is excellent not only in whiteness of a background but also in storage property for a background and an image, and further has excellent dynamic sensitivity. In order to achieve the object, a phenol compound represented by Formula (I) [wherein $R^1$ represents a hydroxyl group or a halogen atom, p represents 0 or an integer of 1 to 5, $R^2$ and $R^3$ each independently represent a hydrogen atom or a $C_1$-$C_6$ alkyl group, $R^4$ represents a hydrogen atom, a $C_1$-$C_6$ alkyl group, an optionally substituted phenyl group or an optionally substituted benzyl group; and a bond shown with a wavy line represents E- or Z-form, or a mixture thereof] and having a color space b* of 10 or less, and preferably having brightness by Hunter of 75 or more, is used as a recording material.

7 Claims, 1 Drawing Sheet

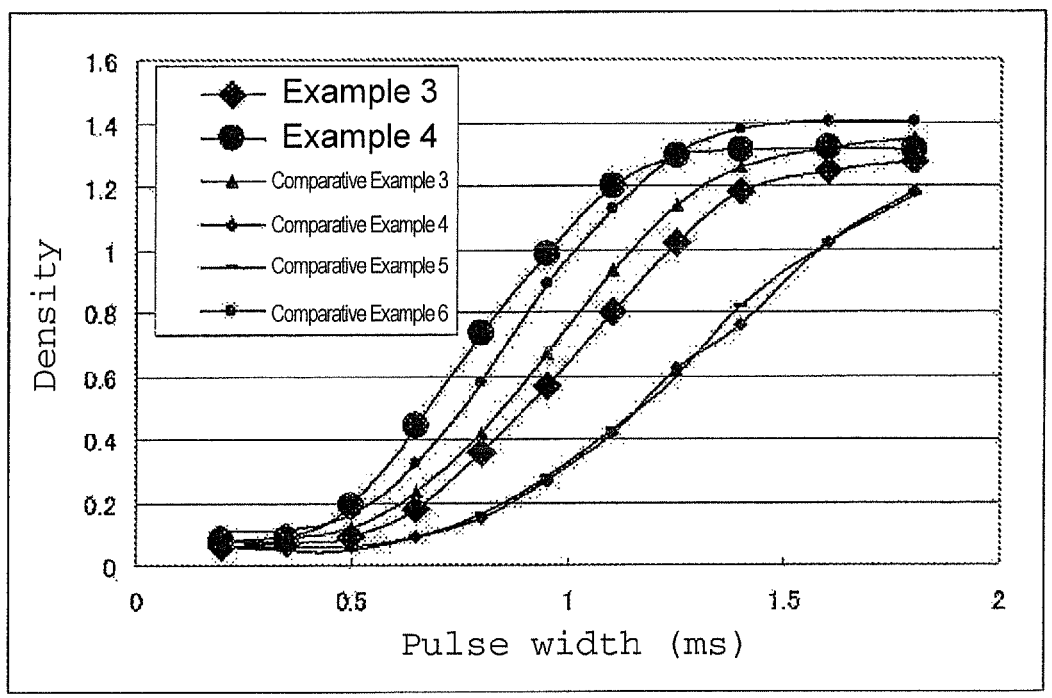

RECORDING MATERIAL USING PHENOL COMPOUND

TECHNICAL FIELD

The present invention relates to a thermal or pressure sensitive recording material utilizing color development caused through a reaction between a color former and a color developer.

This application claims the benefit of priority of the prior Japanese Patent Application No. 2010-195363, filed on Sep. 1, 2010, the entire contents of which are incorporated herein by reference.

BACKGROUND ART

Recording materials utilizing color development caused through a reaction between a color former and a color developer are widely used as thermal recording paper for outputting/recording by a facsimile, a printer or the like, as pressure sensitive copying paper for simultaneously making a plurality of document copies, or the like, because recording processing may be conducted with such recording materials without performing complicated processing such as developing and fixing processing in a short period of time by using a comparatively simple apparatus. Such recording materials are desired to rapidly develop a color, retain whiteness in a portion with no color developed (hereinafter referred to as the "background") and obtain a color developed image with high fastness, and from the viewpoint of long-term storage stability, particularly a recording material excellent in light resistance of the background is demanded. Therefore, various efforts have been exerted to develop color former, color developer, stabilizer and the like, but a sufficiently satisfactory recording material well-balanced in dynamic sensitivity, storage property for a background and an image and the like has not been found yet.

Although 2,4'-dihydroxydiphenylsulfone and 4-hydroxy-4'-isopropoxydiphenylsulfone are conventionally known as recording materials excellent in storage property for a background, the light resistance of the background attained by them is not satisfactory yet.

The present inventors have already proposed a recording material excellent in light resistance of a background and using a cinnamic acid amide-based compound as a color developer (see patent document 1), but obtained crystal of this compound is colored in yellow and hence is not sufficiently satisfactory, and thus, a practical recording material has not been attained yet.

PRIOR ART DOCUMENTS

Patent Documents

Patent document 1: Japanese unexamined Patent Application Publication No. 2003-305959

SUMMARY OF THE INVENTION

Object to be Solved by the Invention

An object of the present invention is to provide a recording material or a recording sheet that is capable of improving the aforementioned disadvantages of conventional recording materials, is excellent not only in whiteness of a background but also in storage property for a background and an image and has excellent dynamic sensitivity.

Means to Solve the Object

The present inventors have found that a recording material excellent in storage property for a background and an image and further having excellent dynamic sensitivity may be obtained by using, as a color developer, the precedently found cinnamic acid amide-based compound in which an amide group and a hydroxyl group are made to be positioned in ortho positions, and have further found that the coloring of obtained crystal, that is, a fatal defect, may be thus avoided, resulting in achieving the present invention relating to a color developer excellent in whiteness of a background.

Specifically, the present invention relates to:

(1) a phenol compound represented by Formula (I):

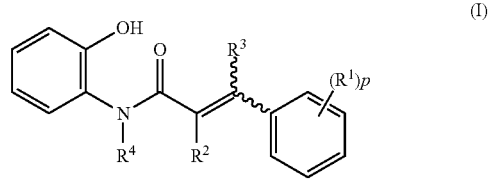

[wherein $R^1$ represents a hydroxyl group, a halogen atom, a $C_1$-$C_6$ alkyl group or a $C_1$-$C_6$ alkoxy group, p represents 0 or an integer of 1 to 5, $R^2$ and $R^3$ each independently represent a hydrogen atom or a $C_1$-$C_6$ alkyl group, $R^4$ represents a hydrogen atom, a $C_1$-$C_6$ alkyl group, an optionally substituted phenyl group or an optionally substituted benzyl group; and a bond shown with a wavy line represents E- or Z-form, or a mixture thereof], wherein the phenol compound has a color space b* of 10 or less, (2) the phenol compound according to (1), wherein the phenol compound has brightness by Hunter of 75 or more, (3) the phenol compound according to (1) or (2), wherein the phenol compound is a compound obtained by a reaction of a purified compound represented by Formula (II):

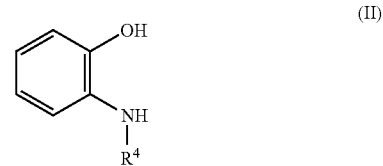

[wherein $R^4$ has the same meaning as defined in Formula (I) above] with a compound represented by Formula (III):

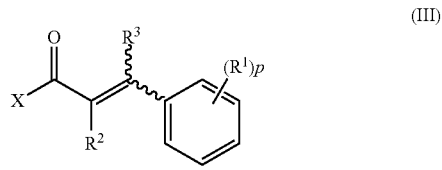

[wherein $R^1$ to $R^3$ and p have the same meaning as defined in Formula (I) above, and X represents a hydroxyl group or a halogen atom] in the presence of a base, followed by crystallization, (4) the phenol compound according to (3), wherein the base is a weak alkaline inorganic compound, (5) the phenol compound according to (3) or (4), wherein the crystallization is conducted by using a polar solvent as a crystallization solvent, (6) a recording material comprising a color former and at least one phenol compound according to (1) to (5), and (7) a recording sheet comprising, on a support, a recording material layer made of a recording material according to (6).

BRIEF DESCRIPTION OF DRAWINGS

FIG. 1 is a diagram illustrating results of test examples for dynamic sensitivity.

MODE OF CARRYING OUT THE INVENTION

Phenol Compound Represented by Formula (I)

A phenol compound represented by Formula (I) will now be described.

In Formula (I), $R^1$ represents a hydrogen atom; a halogen atom such as a fluorine atom, a chlorine atom, a bromine atom or an iodine atom; a linear, branched or cyclic $C_1$-$C_6$ alkyl group such as methyl, ethyl, propyl, isopropyl, butyl, isobutyl, sec-butyl, tert-butyl, pentyl, isopentyl, neopentyl, hexyl, isohexyl, cyclopropyl, cyclobutyl, 2-methylcyclopropyl, cyclopropylmethyl, cyclopentyl or cyclohexyl; or a linear, branched or a cyclic $C_1$-$C_6$ alkoxy group such as methoxy, ethoxy, propoxy, isopropoxy, butoxy, isobutoxy, sec-butoxy, tert-butoxy, pentyloxy, isopentyloxy, hexyloxy, cyclopropoxy, cyclobutoxy, 2-methylcyclopropoxy, cyclopropylmethoxy, cyclopentyloxy or cyclohexyloxy, and preferably represents a hydrogen atom.

$R^2$ and $R^3$ each independently represent a hydrogen atom; or a linear, branched or cyclic $C_1$-$C_6$ alkyl group such as methyl, ethyl, propyl, isopropyl, butyl, isobutyl, sec-butyl, tert-butyl, pentyl, isopentyl, neopentyl, hexyl, isohexyl, cyclopropyl, cyclobutyl, 2-methylcyclopropyl, cyclopropylmethyl, cyclopentyl or cyclohexyl, and each preferably represent a hydrogen atom.

$R^4$ represents a hydrogen atom; a linear, branched or a cyclic $C_1$-$C_6$ alkyl group such as methyl, ethyl, propyl, isopropyl, butyl, isobutyl, sec-butyl, tert-butyl, pentyl, isopentyl, neopentyl, hexyl, isohexyl, cyclopropyl, cyclobutyl, 2-methylcyclopropyl, cyclopropylmethyl, cyclopentyl or cyclohexyl; an optionally substituted phenyl group; or an optionally substituted benzyl group.

Here, examples of a substituent for an "optionally substituted group" are a hydroxyl group; halogen atoms such as a fluorine atom, a chlorine atom, a bromine atom and an iodine atom; $C_1$-$C_6$ alkyl groups such as a methyl group, an ethyl group, an n-propyl group, an isopropyl group, an n-butyl group, a sec-butyl group, a t-butyl group, an n-pentyl group, an isopentyl group, a neopentyl group, a t-pentyl group, an n-hexyl group, an isohexyl group, a 1-methylpentyl group and a 2-methylpentyl group; and $C_1$-$C_6$ alkoxy groups such as a methoxy group, an ethoxy group, an n-propoxy group, an isopropoxy group, an n-butoxy group, a sec-butoxy group and a t-butoxy group.

Incidentally, the compound represented by Formula (I), namely, the compound of the present invention, has geometric isomers as shown below, and depending upon reaction conditions and a purification method, only one isomer is obtained in some cases and a mixture of isomers is obtained in the other cases. These isomers are all embraced in the scope of the present invention.

A typical example of the compound represented by Formula (I) is N-(2-hydroxyphenyl)-cinnamoylamide.

(Production Method for Phenol Compound Represented by Formula (I))

The compound represented by Formula (I) used in the present invention may be obtained by a reaction of a purified compound represented by Formula (II):

(II)

[wherein $R^4$ has the same meaning as defined in Formula (I) mentioned above] with a compound represented by Formula (III):

(III)

[wherein $R^1$ to $R^3$ and p have the same meaning as defined in Formula (I) mentioned above, and X represents a hydroxyl group or a halogen atom] in an organic solvent in the presence of a base.

Here, examples of the halogen atom are the same as those defined with respect to $R^1$ in Formula (I) mentioned above.

The organic solvent is not particularly limited as far as it is inert to the compound represented by Formula (II) or Formula (III), and examples of the organic solvent are alcohols such as methanol, ethanol and isopropanol, ketones such as acetone, nitriles such as acetonitrile, ethers such as tetrahydrofuran and dioxane, and amides such as N,N-dimethylformamide and N,N-dimethylacetamide. Alternatively, a solvent mixed with water may be used. Preferably, an acetone-water mixed solvent is used.

The base is not particularly limited, and examples of the base are organic bases such as pyridine and triethylamine, and weak alkaline inorganic compounds such as sodium carbonate, sodium hydrogencarbonate, potassium carbonate, potassium hydrogencarbonate, ammonium carbonate and ammonium hydrogencarbonate. Preferably, sodium hydrogencarbonate is used.

In the reaction with the compound represented by Formula (III), it may be dissolved in the solvent precedently or may be used as it is. Besides, it may be intermittently added little by little or may be added dropwise, but since the reaction is an exothermic reaction, it is unpreferable to add the compound at a time because heat is immediately generated.

The structure of the compound represented by Formula (I) may be attributed through NMR or the like and its purity may be calculated through liquid chromatography, gas chromatography or the like.

(Requisites for Obtaining Phenol Compound Represented by Formula (I) Having High Whiteness)

In the production of a compound represented by Formula (I) (hereinafter referred to as the cinnamic acid amide-based compound), even when it was confirmed through various analyses including gas chromatography that a compound represented by Formula (II) (hereinafter referred to as the 2-aminophenol compound) had high purity, the cinnamic acid amide-based compound was colored in some cases. Furthermore, a cinnamic acid amide-based compound produced by using a 2-aminophenol compound having been stored for a long period of time was also colored. Moreover, a cinnamic acid amide-based compound got colored when stored for a long period of time even though it was not colored immediately after production. The cause of such coloring was earnestly studied, resulting in finding that there are three requisites for obtaining an uncolored cinnamic acid amide-based compound.

(First Requisite)

The first requisite is to purify a 2-aminophenol compound. This purification may be conducted specifically by a method described in "Purification method for 2-aminophenol compound" described later.

(Second Requisite)

Through the reaction of a 2-aminophenol compound and any of compounds represented by Formula (III) (hereinafter referred to as cinnamic acids), not only a cinnamic acid amide-based compound but also a by-product HX is obtained. When X is a halogen compound, HX is an acidic substance. HX may form a salt together with an amino group of the 2-aminophenol compound. The amino group having formed the salt is difficult to react with the cinnamic acids. Therefore, it is necessary to trap the by-product HX with an alkali compound. As this alkali compound, the 2-aminophenol compound may be used. In this case, however, since the 2-aminophenol compound is necessary for the reaction in a molar amount twice or more of the cinnamic acid amide-based compound, merely a half or less of the used 2-aminophenol compound is reacted as a result, and therefore, the use of this compound for this purpose is economically unsuitable.

Therefore, the excessive amount of the 2-aminophenol compound may be replaced with an inexpensive alkaline inorganic compound. When a strong alkaline inorganic compound such as sodium hydroxide is used, however, the raw material compound is unpreferably discolored. Accordingly, the second requisite is to use a weak alkaline inorganic compound as the alkaline inorganic compound. Examples of the weak alkaline inorganic compound are sodium carbonate, sodium hydrogencarbonate, potassium carbonate, potassium hydrogencarbonate, ammonium carbonate and ammonium hydrogencarbonate.

(Third Requisite)

The third requisite is to use a polar solvent as a crystallization solvent, and furthermore, to wash obtained crystal with a polar solvent, water, or a mixed solvent of a polar solvent and water. As a specific exemplary process for crystallization, a polar solvent and water are added to a prepared cinnamic acid amide-based compound and dissolved therein by heating once, the resultant solution is cooled for separating out crystal, and the crystal is sufficiently washed with water. Examples of the polar solvent are alcohols such as methanol and ethanol, ketones such as acetone, and nitriles such as acetonitrile. Alternatively, the crystallization solvent may be a mixed solvent of a polar solvent and water. Furthermore, the crystallization is performed preferably by using water having been acidified by a mineral acid such as hydrochloric acid. Moreover, before the crystallization process, processing for adding an organic solvent separable from water and water (or water having been acidified by a mineral acid such as hydrochloric acid) and separating an aqueous layer may be performed. However, in case of using a mixed solvent of a polar solvent and a nonpolar solvent, the high proportion of the nonpolar solvent is not preferable because a coloring component or a causative component for coloring may not be removed.

Among these first to third requisites, it is always necessary to satisfy the first requisite, but the second and third requisites should not be always satisfied but are preferably satisfied. In the case where none of the requisites is satisfied, however, a prepared cinnamic acid amide-based compound is colored or gets colored when stored for a long period of time even when it is not colored immediately after the production. Accordingly, a compound represented by Formula (I) not getting colored for a long period of time may not be obtained until these requisites are satisfied.

(Purification Method for 2-Aminophenol Compound)

A 2-aminophenol (o-aminophenol) compound used as a raw material for a cinnamic acid amide-based compound of the present invention may be purchased as a purified product or may be obtained by purifying an unpurified product purchased. The purification method is not particularly limited, but purification such as reduction purification using a reductant, sublimation purification, purification through recrystallization, separation purification with a silica gel or the like, adsorption removal purification with activated carbon or the like, or separation purification through separation of an organic solvent and water may be employed for obtaining a purified 2-aminophenol compound.

The reductant used in the purification is not particularly limited, and examples of the reductant are sulfites such as sodium sulfite and potassium sulfite, thiosulfates such as sodium thiosulfate and potassium thiosulfate, dithionites such as sodium hydrosulfite, potassium hydrosulfite and hydrates thereof, hydrazine, metal halide salts such as tin dichloride, and boron compounds such as sodium borohydride.

In order to obtain a cinnamic acid amide-based compound with high whiteness according to the present invention, it is preferable not only to use a purified 2-aminophenol compound as described above as a raw material but also to wash prepared crystal under an acidic condition after producing the cinnamic acid amide-based compound.

An acid to be used for attaining the acidic condition is not particularly limited, and acids such as hydrochloric acid, sulfuric acid or phosphoric acid may be used, among which hydrochloric acid is preferably used.

Examples of a method for attaining the acidic condition are a method in which an acid is added after completing the reaction, a method in which an acid is added before separating the crystal, and a method in which an acidic solvent is used for washing the crystal, among which the method in which an acid is added after completing the reaction is preferably employed.

The amount of the acid is not particularly limited and may be an amount sufficient for attaining the acidic condition.

The purification for removing a colored substance may be performed by, but not limited to, any one of or both of a method in which a 2-aminophenol compound used as a raw material is purified and a method in which a cinnamic acid amide-based compound is purified. In employing a method in which an unpurified 2-aminophenol is used as a raw material and a resultant cinnamic acid amide-based compound having got colored is purified, the purification through recrystallization alone is not sufficient and hence it is necessary to employ a combination of a plurality of purification methods. Preferably, the 2-aminophenol compound is reduction purified by using a reductant and the crystal of the cinnamic acid amide-based compound is washed under the acidic condition.

(Measured Values for Whiteness and the Like)

A color developer is applied on a substrate such as paper together with a color former and the like, and the resultant is used as thermal recording paper. Thermal recording paper is demanded, as a product, to be whiter before color development. Therefore, a color developer is required to be whiter. Furthermore, the degree of the white color may be measured with a spectrophotometer. A typical measured value for whiteness is indicated by brightness by Hunter (a W value). Besides, color spaces may be indicated on the basis of JIS Z 8729 by using the L*a*b* chromatic system (as L*, a* and b*).

A color developer excellent in the whiteness and the color spaces a* and b* in particular is preferred. Specifically, brightness by Hunter of 75 or more is sufficient and of 79 or more is practically preferable. Also, a color space a* in a range of −5 or more and 0 or less is sufficient and in a range of −3 or more and 0 or less is practically preferable, and a color space b* in a range of 0 or more and 10 or less is sufficient and in a range of 0 or more and 8 or less is practically preferable.

The whiteness is indicated by brightness by Hunter (a W value).

The brightness by Hunter, the color spaces L*, a* and b* may be measured as follows:

A sample is filled in an accessory cell for powder measurement of a spectrophotometer (SD 5000 or SE 2000, manufactured by Nippon Denshoku Industries, Co., Ltd.) so as not to transmit light, and measurement is performed under a room temperature atmosphere with a measuring diameter set to 28 mm.

(Recording Material)

A recording material of the present invention may be put to any uses as far as it comprises a color former and at least one phenol compound represented by Formula (I), and may be used, for example, as a thermal recording material, a pressure sensitive copying material and the like.

A use ratio of the compound represented by Formula (I) to the color former is generally 0.01 to 10 parts by mass, preferably 0.5 to 10 parts by mass and further preferably 1.0 to 5 parts by mass based on 1 part by mass of the color former.

(Other Components of Recording Material)

The recording material of the present invention may comprise, in addition to the color former and the compound represented by Formula (I), one or more of known color developers, image stabilizers, sensitizers, fillers, dispersants, antioxidants, desensitizers, anti-adhesion agents, anti-foam agents, light stabilizers, fluorescent brightening agents and the like if necessary. The content of each of these other components generally ranges from 0.1 to 15 parts by mass and preferably 1 to 10 parts by mass based on 1 part by mass of the color former.

These agents may be included in a color developing layer, and when the recording material has a multilayered structure, they may be included in an arbitrary layer, for example, in a protection layer. Particularly when an overcoat layer or an undercoat layer is provided above and/or below the color developing layer, such layers may include an antioxidant, a light stabilizer or the like. Furthermore, an antioxidant and a light stabilizer may be included in such a layer in a state encapsulated in a microcapsule if necessary.

Examples of the color former used in a recording material of the present invention are leuco dyes such as fluoran-based, phthalide-based, lactam-based, triphenylmethane-based, phenothiazine-based and spiropyran-based dyes. The color former is not limited to these dyes but any color former may be used as far as it develops a color when brought into contact with a color developer that is an acidic substance. Furthermore, it goes without saying that one of these color formers may be singly used for producing a recording material of a color developed by the used color former, or a mixture of two or more of them may be used. For example, a mixture of color formers of three primary colors of red, blue and green or a black color former may be used for producing a recording material for developing a real black color.

Example of the fluoran-based color former are 3,3-bis(p-dimethylaminophenyl)-phthalide, 3,3-bis(p-dimethylaminophenyl)-6-dimethylaminophthalide (having another name of crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluorane, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzfluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluoromethylphenyl)amino}-6-diethylaminofluoran, 2-{3,6-bis(diethylamino)-9-(o-chloroanilino)xanthyl benzoic acid lactam}, 3-diethylamino-6-methyl-7-(m-trichloromethylanilino)fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-pyrrolidino-6-methyl-7-anilinofluoran, 3-piperidino-6-methyl-7-anilinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-diethylamino-5-methyl-7-benzylaminofluoran, 3-diethylamino-5-chlorofluoran, 3-diethylamino-6-(N,N'-dibenzylamino)fluoran, 3,6-dimethoxyfluoran, 2,4-dimethyl-6-(4-dimethylaminophenyl)aminofluoran, 3-diethylamino-7-(m-trifluoromethylanilino)fluoran, 3-diethylamino-6-methyl-7-octylaminofluoran, 3-diethylamino-6-methyl-7-(m- tolylamino)fluoran, 3-diethylamino-6-methyl-7-(2,4-xylylamino)fluoran, 3-diethylamino-7-(o-fluoroanilino) fluoran, 3-diphenylamino-6-methyl-7-anilinofluoran, benzoyl leuco methylene blue, 6'-chloro-8'-methoxy-benzoindolino-spiropyran, 6'-bromo-3'-methoxy-benzoindolino-spiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl) phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-4'-chloro-5'-methylphenyl)phthalide, 3-morphorino-7-(N-propyl-trifluoromethylanilino)fluoran, 3-pyrrolidino-7-trifluoromethylanilino)fluoran, 3-diethylamino-5-chloro-7-(N-benzyl-trifluoromethylanilino)fluoran, 3-pyrrolidino-7-(di-p-chlorophenyl)methylaminofluoran, 3-diethylamino-5-chloro-7-($\alpha$-phenylethylamino)fluoran, 3-(N-ethyl-p-toluidino)-7-($\alpha$-phenylethylamino)fluoran, 3-diethylamino-7-(o-methoxycarbonylphenylamino)fluoran, 3-diethylamino-5-methyl-7-($\alpha$-phenylethylamino)fluoran, 3-diethylamino-7-piperidinofluoran, 2-chloro-3-(N-methyl-toluidino)-7-(p-n-butylanilino)fluoran, 3-(N-methyl-N-isopropylamino)-6-methyl-7-anilinofluoran, 3-dibutylamino-6-methyl-7-anilinofluoran, 3-dipentylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-$\alpha$-naphthylamino-4'-bromofluoran, 3-diethylamino-6-chloro-7-anilinofluoran, 3-N-ethyl-N-(2-ethoxypropyl)amino-6-methyl-7-anilinofluoran, 3-N-ethyl-N-tetrahydrofurfurylamino-6-methyl-7-anilinofluoran, 3-diethylamino-6-methyl-7-mesitidino-4',5'-benzofluoran, and 3-(N-ethyl-p-toluidino)-7-(methylphenylamino)fluoran.

Among these color formers, preferable ones are 3-bis(p-dimethylaminophenyl)-6-dimethylaminophthalide, 3-cyclohexylamino-6-chlorofluoran, 3-diethylamino-7-chlorofluoran, 3-diethylamino-6,8-dimethylfluoran, 3-diethylamino-7-methylfluoran, 3-diethylamino-7,8-benzfluoran, 3-diethylamino-6-methyl-7-chlorofluoran, 3-dibutylamino-6-methyl-7-bromofluoran, 3-diethylamino-7-(o-chloroanilino)fluoran, 3-dibutylamino-7-(o-chloroanilino)fluoran, 3-N-methyl-N-cyclohexylamino-6-methyl-7-anilinofluoran, 3-(0,0-diethylamino)-5-methyl-7-(N/N-dibenzylamino) fluoran, 3-(N,N-diethylamino)-7-(N,N-dibenzylamino)fluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-7-(o-fluoroanilino)fluoran, 3-diphenylamino-6-methyl-7-anilinofluoran, benzoyl leuco methylene blue, 3-dibutylamino-6-methyl-7-anilinofluoran, 3-N-ethyl-N-tetrahydrofurfurylamino-6-methyl-7-anilinofluoran and 3-(N-ethyl-p-toluidino)-7-(methylphenylamino)fluoran.

Examples of a near infrared absorbing dye are 3-[4-[4-(4-anilino)-anilino]anilino]-6-methyl-7-chlorofluoran, 3,3-bis[2-(4-dimethylaminophenyl)-2-(4-methoxyphenyl)vinyl]-4,5,6,7-tetrachlorophthalide, and 3,6,6'-tris(dimethylamino) spiro(fluorene-9,3'-phthalide).

The compound represented by Formula (I) of the present invention may be suitably used as a color developer principally for a thermal recording material, and the compound may be singly used or may be used in combination with a plurality of known color developers. In this case, a ratio among them is arbitrary.

Specific examples of other color developers are:

bisphenol compounds such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl) hexane, 2,2-bis(4-hydroxyphenyl)propane, 2,2-bis(4-hydroxyphenyl)butane, 2,2-bis(4-hydroxy-3-methylphenyl) propane, 4,4'-(1-phenylethylidene)bisphenol, 4,4'-ethylidenebisphenol, (hydroxyphenyl)methylphenol, 2,2'-bis (4-hydroxy-3-phenyl-phenyl)propane, 4,4'-(1,3-phenylenediisopropylidene)bisphenol, 4,4'-(1,4-phenylenediisopropylidene)bisphenol and 2,2-bis(4-hydroxyphenol)butyl acetate; sulfur-containing bisphenol compounds such as 4,4'-dihydroxydiphenylthioether, 1,7-di (4-hydroxyphenylthio)-3,5-dioxaheptane, 2,2'-bis(4-hydroxyphenylthio)diethylether and 4,4'-dihydroxy-3,3'-dimethyldiphenylthio ether; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chrolobenzyl 4-hydroxybenzoate, methylbenzyl 4-hydroxybenzoate and diphenylmethyl 4-hydroxybenzoate; benzoic acid metal salts such as zinc benzoate and zinc 4-nitrobenzoate; salicylic acids such as 4-[2-(4-methoxyphenyloxy)ethyloxy]salicylic acid; salicylic acid metal salts such as zinc salicylate and zinc bis[4-(octyloxycarbonylamino)-2-hydroxybenzoate]; hydroxysulfones such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 4-allyloxy-4'-hydroxydiphenylsulfone, 2-(4-hydroxyphenylsulfonyl) phenol, 4,4'-sulfonylbis[2-(2-propenyl)]phenol, 4-[{4-(propoxy)phenyl}sulfonyl]phenol, 4-[{4-(allyloxy) phenyl}sulfonyl]phenol, 4-[{4-(benzyloxy)phenyl}sulfonyl] phenol, and 2,4-bis(phenylsulfonyl)-5-methyl-phenol; multivalent metal salts of hydroxysulfones such as 4-phenylsulfonylphenoxy zinc, 4-phenylsulfonylphenoxy magnesium, 4-phenylsulfonylphenoxy aluminum and 4-phenylsulfonylphenoxy titanium; 4-hydroxyphthalic acid diesters such as dimethyl 4-hydroxyphthalate, dicyclohexyl 4-hydroxyphthalate and diphenyl 4-hydroxyphthalate; hydroxynaphthoic acid esters such as 2-hydroxy-6-carboxynaphthalene; trihalomethylsulfones such as tribromomethylphenylsulfone; sulfonylureas such as 4,4'-bis(p-toluenesulfonylaminocarbonylamino)diphenylmethane and N-(4-methylphenylsulfonyl)-N'-(3-(4-methylphenylsulfonyloxy)phenyl)urea; hydroxyacetophenone, p-phenylphenol, benzyl 4-hydroxyphenylacetate, p-benzylphenol, hydroquinone-monobenzyl ether, 2,4-dihydroxy-2'-methoxybenzanilide, tetracyanoquinodimethanes, N-(2-hydroxyphenyl)-2-[(4-hydroxyphenyl)thio]acetamide, N-(4-hydroxyphenyl)-2-[(4-hydroxyphenyl)thio]acetamide, 4-hydroxybenzenesulfonanilide, 4'-hydroxy-4-methylbenzenesulfonanilide, 4,4'-bis(4-methyl-3-phenoxycarbonyl)aminophenylureide))diphenylsulfone, 3-(3-phenylureide)benzenesulfonanilide, octadecyl phosphate, dodecyl phosphate; and diphenylsulfone crosslinking compounds represented by the following formula, and a mixture thereof:

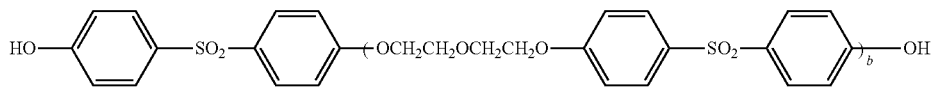

(b represents an integer of 0 to 6)

Among these exemplified substances, preferable examples are 4-hydroxy-4'-isopropoxydiphenylsulfone, the diphenylsulfone crosslinking compounds and a mixture thereof.

Examples of the image stabilizer are epoxy group-containing diphenylsulfones such as 4-benzyloxy-4'-(2-methylglycidyloxy)-diphenylsulfone and 4,4'-diglycidyloxydiphenylsulfone; 1,4-diglycidyloxybenzene, 4-[α-(hydroxymethyl) benzyloxy]-4'-hydroxydiphenylsulfone, a 2-propanol derivative, a salicylic acid derivative and a metal salt (especially zinc salts) of an oxynaphthoic acid derivative, a metal salt of 2,2-methylenebis(4,6-t-butylphenyl)phosphate, other water-insoluble zinc compounds, hindered phenol compounds such as 2,2-bis(4'-hydroxy-3',5'-dibromophenyl)propane, 4,4'-sulfonylbis(2,6-dibromophenol), 4,4'-butylidene (6-t-butyl-3-methylphenol), 2,2'-methylene-bis(4-methyl-6-t-butylphenol), 2,2'-methylene-bis(4-ethyl-6-t-butylphenol), 2,2'-di-t-butyl-5,5'-dimethyl-4,4'-sulfonyldiphenol, 1,1,3-tris(2-methyl-4-hydroxy-5-cyclohexylphenyl)butane and 1,1,3-tris(2-methyl-4-hydroxy-5-t-butylphenyl)butane, phenol novolac compounds and epoxy resins.

It is noted that the image stabilizer is preferably in a solid state at ordinary temperature, and is particularly preferably a compound having a melting point of 60° C. or more and minimally dissolved in water.

Examples of the sensitizer are higher fatty acid amides such as stearic acid amide, stearic acid anilide and palmitic acid amide; amides such as benzamide, acetoacetanilide, thioacetanilide acrylic acid amide, ethylenebisamide, orthotoluene sulfonamide and para-toluene sulfonamide; phthalic acid diesters such as dimethyl phthalate, dibenzyl isophthalate, dimethyl isophthalate, dimethyl terephthalate, diethyl isophthalate, diphenyl isophthalate and dibenzyl terephthalate; oxalic acid diesters such as dibenzyl oxalate, di(4-methylbenzyl) oxalate, di(4-chlorobenzyl) oxalate, an equal volume mixture of benzyl oxalate and di(4-chlorobenzyl) oxalate, and an equal volume mixture of di(4-chlorobenzyl) oxalate and di(4-methylbenzyl) oxalate; bis(t-butyl phenols) such as 2,2'-methylenebis(4-methyl-6-t-butyl phenol) and 4,4'-methylene-bis-2,6-di-t-butyl phenol; diethers of 4,4'-dihydroxydiphenylsulfone such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone and 4,4'-diallyloxydiphenylsulfone; diethers of 2,4'-dihydroxydiphenylsulfone such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, 2,4'-dihexyloxydiphenylsulfone and 2,4'-diallyloxydiphenylsulfone;
1,2-bis(phenoxy)ethane, 1,2-bis(4-methylphenoxy)ethane, 1,2-bis(3-methylphenoxy)ethane, 1,2-bis(phenoxymethyl) benzene, 1,2-bis(4-methoxyphenylthio)ethane, 1,2-bis(4-methoxyphenoxy)propane, 1,3-phenoxy-2-propanol, 1,4-diphenylthio-2-butene, 1,4-diphenylthiobutane, 1,4-diphenoxy-2-butene, 1,5-bis(4-methoxyphenoxy)-3-oxapentane, 1,3-dibenzoyloxypropane, dibenzoyloxymethane, 4,4'-ethylenedioxy-bis-benzoic acid dibenzyl ester, bis-[2-(4-methoxy-phenoxy)ethyl]ether, 2-naphthylbenzyl ether, 1,3-bis(2-vinyloxyethoxy)benzene, 1,4-diethoxynaphthalene, 1,4-dibenzyloxynaphthalene, 1,4-dimethoxynaphthalene, 1,4-bis(2-vinyloxyethoxy)benzene, p-(2-vinyloxyethoxy)biphenyl, p-aryloxybiphenyl, p-propargyloxybiphenyl, p-benzyloxybenzyl alcohol, 4-(m-methylphenoxymethyl)biphenyl, 4-methylphenyl-biphenyl ether, di-β-naphthylphenylenediamine, diphenylamine, carbazole, 2,3-di-m-tolylbutane, 4-benzylbiphenyl, 4,4'-dimethylbiphenyl,
terphenyls such as m-terphenyl and p-terphenyl; 1,2-bis(3,4-dimethylphenyl)ethane, 2,3,5,6-tetramethyl-4'-methyldiphenylmethane, 4-acetylbiphenyl, dibenzoylmethane, triphenylmethane, phenyl 1-hydroxy-naphthoate, methyl 1-hydroxy-2-naphtoate, N-octadecylcarbamoyl-p-methoxycarbonylbenzene, benzyl p-benzyloxybenzoate, phenyl β-naphthoate, methyl p-nitrobenzoate, diphenyl sulfone,
carbonic acid derivatives such as diphenyl carbonate, guaiacol carbonate, di-p-tolyl carbonate and phenyl-α-naphthyl carbonate;
1,1-diphenyl propanol, 1,1-diphenyl ethanol, N-octadecylcarbamoyl benzene, dibenzyldisulfide, stearic acid and Amide AP-1 (a 7:3 mixture of stearic acid amide and palmitic acid amide),
stearates such as aluminum stearate, calcium stearate and zinc stearate; zinc palmitate, behenic acid, zinc behenate, montanic acid wax and polyethylene wax.

Preferable examples are 2-naphthylbenzyl ether, m-terphenyl, 4-benzylbiphenyl, benzyl oxalate, di(4-chlorobenzyl) oxalate, an equal volume mixture of benzyl oxalate and di(4-chlorobenzyl) oxalate, di(4-methylbenzyl) oxalate, an equal volume mixture of di(4-chlorobenzyl) oxalate and di(4-methylbenzyl) oxalate, phenyl 1-hydroxy-2-naphthoate, 1,2-bis (phenoxy)ethane, 1,2-bis(3-methylphenoxy)ethane, 1,2-bis (phenoxymethyl)benzene, dimethyl terephthalate, stearic acid amide, Amide AP-1 (a 7:3 mixture of stearic acid amide and palmitic acid amide), diphenyl sulfone and 4-acetylbiphenyl.

More preferable examples are di(4-methylbenzyl) oxalate, 1,2-bis(3-methylphenoxy)ethane, 1,2-bis(phenoxymethyl) benzene, diphenyl sulfone and 2-naphthylbenzyl ether.

Examples of the filler are silica, clay, kaolin, fired kaolin, talc, satin white, aluminum hydroxide, calcium carbonate, magnesium carbonate, zinc oxide, titanium oxide, barium sulfate, magnesium silicate, aluminum silicate, a plastic pigment, diatomite, talc and aluminum hydroxide. Among these examples, fired kaolin and calcium carbonate are suitably used. The filler is included in a content of 0.1 to 15 parts by mass and preferably 1 to 10 parts by mass based on 1 part by mass of the color former. Besides, a mixture of the above-described fillers may be used.

Examples of the dispersant are polyvinyl alcohol; polyvinyl alcohols of various saponification degrees and polymerization degrees such as acetoacetylated polyvinyl alcohol, carboxy-denatured polyvinyl alcohol, sulfonic acid-denatured polyvinyl alcohol, amide-denatured polyvinyl alcohol and butyral-denatured polyvinyl alcohol; cellulose derivatives such as methylcellulose, carboxymethylcellulose, hydroxyethylcellulose, ethylcellulose, acetylcellulose and hydroxymethylcellulose; sodium polyacrylate, polyacrylic acid ester, polyacrylamide, starch, sulfosuccinic acid esters such as dioctylsodium sulfosuccinate, sodium dodecylbenzenesulfonate, sodium salt of lauryl alcohol sulfuric acid ester, a fatty acid salt, a styrene-maleic anhydride copolymer, a styrene-butadiene copolymer, polyvinyl chloride, polyvinyl acetate, polyacrylic acid ester, polyvinyl butyral, polyurethane, polystyrene and copolymers thereof, a polyamide resin, a silicone resin, a petroleum resin, a terpene resin, a ketone resin and a coumarone resin.

The dispersant may be dissolved in a solvent such as water, alcohol, ketone, ester or hydrocarbon for use, or may be dispersed in water or another solvent in an emulsion or paste state for use.

Examples of the antioxidant are 2,2'-methylenebis(4-methyl-6-t-butylphenol), 2,2'-methylenebis(4-ethyl-6-t-butylphenol), 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, 1,1,3-tris(2-methyl-4-hydroxy-5-cyclohexylphenyl)butane, 2,2'-methylenebis(6-tert-butyl-4-methylphenol), 2,2'-methylenebis(6-tert-butyl-4-ethylphenol), 4,4'-thiobis(6-tert-butyl-3-methylphenol), 1,3,5-tris[{4-(1,1-dimethylethyl)-3-hydroxy-2,6-dimethylphenyl}methyl]-1,3,5-triazine-2,4,6(1H,3H,5H)-trione, and 1,3,5-tris[{3,5-bis(1,1-dimethylethyl)-4-hydroxyphenyl}methyl]-1,3,5-triazine-2,4,6(1H,3H,5H)-trione.

Examples of the desensitizing agent are fatty higher alcohol, polyethylene glycol and a guanidine derivative.

Examples of the anti-adhesion agent are stearic acid, zinc stearate, calcium stearate, carnauba wax, paraffin wax and ester wax.

Examples of the anti-foam agent are higher alcohol-based, fatty acid ester-based, oil-based, silicone-based, polyether-based, denatured hydrocarbon-based and paraffin-based antifoam agents.

Examples of the light stabilizer are salicylic acid-based UV absorbers such as phenyl salicylate, p-t-butylphenyl salicylate and p-octylphenyl salicylate; benzophenone-based UV absorbers such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone and bis(2-methoxy-4-hydroxy-5-benzoylphenyl)methane; benzotriazole-based UV absorbers such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-tert-butylphenyl)benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"'-propylhexyl)oxyphenyl]benzotriazole, 2,2'-methylenebis[4-(1,1,3,3-tetramethylbutyl)-6-(2H-benzotriazole-2-yl)]phenol, and a condensate of polyethylene glycol and methyl-3-[3-t-butyl-5-(2H-benzotriazole-2-yl)-4-hydroxyphenyl]propionate; cyanoacrylate-based UV absorbers such as 2'-ethylhexyl-2-cyano-3,3-diphenyl acrylate and ethyl-2-cyano-3,3-diphenyl acrylate; hindered amine-based UV absorbers such as bis(2,2,6,6-tetramethyl-4-piperidyl) sebacate, succinic acid-bis(2,2,6,6-tetramethyl-4-piperidyl) ester and 2-(3,5-di-t-butyl)malonic acid-bis(1,2,2,6,6-pentamethyl-4-piperidyl)ester; and 1,8-dihydroxy-2-acetyl-3-methyl-6-methoxynaphthalene.

Examples of the fluorescent brightening agent are 4,4'-bis[2-anilino-4-(2-hydroxyethyl)amino-1,3,5-triazinyl-6-amino]stilbene-2,2'-disulfonic acid=disodium salt, 4,4'-bis[2-anilino-4-bis(hydroxyethyl)amino-1,3,5-triazinyl-6-amino]stilbene-2,2'-disulfonic acid=disodium salt, 4,4'-bis[2-anilino-4-bis(hydroxypropyl)amino-1,3,5-triazinyl-6-amino]stilbene-2,2'-disulfonic acid=disodium salt, 4,4'-bis[2-methoxy-4-(2-hydroxyethyl)amino-1,3,5-triazinyl-6-amino]stilbene-2,2'-disulfonic acid=disodium salt, 4,4'-bis[2-methoxy-4-(2-hydroxypropyl)amino-1,3,5-triazinyl-6-amino]stilbene-2,2'-disulfonic acid=disodium salt, 4,4'-bis[2-m-sulfoanilino-4-bis(hydroxyethyl)amino-1,3,5-triazinyl-6-amino]stilbene-2,2'-disulfonic acid=disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid=tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid=hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid=hexasodium salt, 4,4'-bis[2-(2,5-disulfoanilino)-4-formalinylamino-1,3,5-triazinyl-6-amino]stilbene-2,2'-disulfonic acid=hexasodium salt and 4,4'-bis[2-(2,5-disulfoanilino)-4-bis(hydroxyethyl)amino-1,3,5-triazinyl-6-amino]stilbene-2,2'-disulfonic acid hexasodium salt.

(Method for Producing Recording Material)

When the present invention is applied to thermal recording paper, the production may be carried out in the same manner as in a conventionally known method, and for example, the thermal recording paper may be produced by dispersing particulates of a compound of the present invention and particulates of a color former respectively in aqueous solutions of a water-soluble binder, such as polyvinyl alcohol or cellulose, so as to give suspension solutions, mixing the suspension solutions, applying the thus obtained mixture onto a support such as paper, and drying the resultant.

When the present invention is applied to pressure sensitive copying paper, the pressure sensitive copying paper may be produced in the same manner as in a case where a known color developer or sensitizer is used. For example, a color former encapsulated in a microcapsule by a known method is dispersed by using an appropriate dispersant, and the thus obtained dispersion is applied onto paper so as to prepare a color former sheet. Furthermore, a dispersion of a color developer is applied onto paper so as to prepare a color developer sheet. The thus prepared sheets are combined to each other to produce pressure sensitive copying paper. The pressure sensitive copying paper may be either a unit consisting of upper paper having a lower face coated with and carrying a microcapsule containing an organic solvent solution of a color former and lower paper having an upper face coated with and carrying a color developer (an acidic substance), or a what is called self-content paper having one face coated with both the microcapsule and the color developer.

As a color developer used in the production or a color developer included in a mixture to be used in the production, conventionally known one may be used, and examples are inorganic acidic substances such as acid clay, activated clay, attapulgite, bentonite, colloidal silica, aluminum silicate, magnesium silicate, zinc silicate, tin silicate, fired kaolin and talc; aliphatic carboxylic acids such as oxalic acid, maleic acid, tartaric acid, citric acid, succinic acid and stearic acid; aromatic carboxylic acids such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3,5-di-t-butylsalicylic acid, 3-methyl-5-benzylsalicylic acid, 3-phenyl-5-(2,2-dimethylbenzyl) salicylic acid, 3,5-di-(2-methylbenzyl)salicylic acid and 2-hydroxy-1-benzyl-3-naphthoic acid, and metallic salts such as zinc, magnesium, aluminum and titanium of these aromatic carboxylic acids; phenol resin-based color developers such as a p-phenylphenol-formalin resin and a p-butylphenol-acetylene resin, and a mixture of such a phenol resin-based color developer and any of the above-mentioned metallic salts of the aromatic carboxylic acids.

The support used in the present invention may be conventionally known paper, synthetic paper, a film, a plastic film, a foamed plastic film, a non-woven fabric or recycled paper such as waste paper pulp. A mixture of them may also be used as the support.

In the case where paper is used as the support, a dispersion including a dispersion of a color former, a dispersion of a color developer and a dispersion of a filler may be directly applied to the paper, or alternatively, the dispersion may be applied after coating the paper with a dispersion for an undercoat layer and drying the resultant. The dispersion is preferably applied after applying the dispersion for an undercoat layer because higher dynamic sensitivity may be thus attained.

The dispersion for an undercoat layer is used for improving the smoothness on the surface of the support and is not particularly limited, and preferably includes a filler, a dispersant and water. Specifically, fired kaolin or calcium carbonate is preferably used as the filler, and polyvinyl alcohol is preferably used as the dispersant.

For forming a recording material layer on a support, a method in which a dispersion including a dispersion of a color former, a dispersion of a color developer and a dispersion of a filler is applied onto a support and the resultant is dried, a method in which the dispersion is sprayed with a sprayer or the like and the resultant is dried, a method in which the support is immersed in the dispersion for a prescribed period of time and the resultant is dried, or the like may be employed.

Furthermore, for applying the dispersion, a hand coating method, a size press coating method, a roll coating method, an air knife coating method, a blend coating method, a blow coating method, a curtain coating method, a comma direct method, a gravure direct method, a gravure reverse method, a reverse roll coating method or the like may be employed.

EXAMPLES

The recording material of the present invention will now be described in detail by way of examples, and it is noted that the present invention is not limited to the following examples.

Example 1

Synthesis of N-(2-hydroxyphenyl)-cinnamoylamide

To a mixture of 75 ml of acetone, 25 ml of water and 4.6 g of sodium hydrogencarbonate, 6.0 g of purified 2-aminophenol (manufactured by Aldrich, purity: 99%) was added, and the resultant mixture was cooled to 5° C. A solution of 8.6 g of cinnamoyl chloride in 10 ml of methylene chloride was added dropwise thereto so as not to elevate the temperature beyond 10° C. After the dropwise addition, a reaction was conducted at room temperature for hours. After completing the reaction, the pH of the thus obtained reaction solution was acidified by adding 2.6 g of 35% hydrochloric acid thereto, and thereafter, the solvent was distilled under reduced pressure. To the thus obtained residue, 50 ml of methanol and 25 ml of water were added, and the resultant mixture was heated to 60° C. once and was cooled to 5° C. The thus separated crystal was filtered off, and the crystal was sufficiently washed with water until the filtrate was colorless. The resultant crystal was dried under reduced pressure, so as to obtain 11.1 g of the target compound as a white crystal (yield: 93% in terms of cinnamoyl chloride).

$^1$H-NMR ($d_6$-DMSO): $\delta$6.79 (dt, 1H), $\delta$6.88 (dd, 1H), $\delta$6.95 (dt, 1H), $\delta$7.16 (d, 1H), $\delta$7.41 (m, 3H), $\delta$7.56 (d, 1H), $\delta$7.63 (d, 2H), $\delta$7.92 (d, 1H), $\delta$9.47 (s, 1H), $\delta$9.96 (bs, 1H).

Melting point: 160-163° C.

Example 2

Purification of 2-Aminophenol by Purification Method Described in Japanese Unexamined Patent Application Publication No. 6-239813 and Synthesis of N-(2-hydroxyphenyl)-cinnamoylamide A homogenous solution was obtained by dispersing 6.0 g of 2-aminophenol with low purity (of 97%) in 20 ml of water and adding 5.7 g of 35% hydrochloric acid thereto. To the solution, 0.1 g of sodium hydrosulfite was added and dissolved therein, the resultant solution was cooled to 10° C., and 7.9 g of 28% sodium hydroxide was slowly added thereto for neutralizing the solution. After addition of 75 ml of acetone and 4.6 g of sodium hydrogencarbonate, the resultant solution was cooled to 5° C. A solution of 8.6 g of cinnamoyl chloride in 10 ml of methylene chloride was added dropwise thereto, and after the temperature was elevated to room temperature, a reaction was conducted for 2 hours. Thereafter, a similar after-treatment to that of Example 1 was conducted, so as to obtain 11.8 g of the target compound as a white crystal (yield: 99% in terms of cinnamoyl chloride). Melting point: 158-163° C.

Example 5

According to the procedure described in Example 1 of Japanese unexamined Patent Application Publication No. 2003-305959, 10.0 g of purified 2-aminophenol (manufactured by Aldrich, purity: 99%) and 7.7 g of cinnamoyl chloride were used to synthesize 8.38 g of N-(2-hydroxyphenyl)-cinnamoylamide (yield: 70.1% in terms of cinnamoyl chloride). The thus obtained crystal was white.

Comparative Example 1

Example 2 was practiced except that sodium hydrosulfite was not added, so as to synthesize N-(2-hydroxyphenyl)-cinnamoylamide. The title compound was obtained as a yellow crystal. The thus obtained crystal was recrystallized from n-hexane/ethyl acetate, but the crystal remained yellow.

Comparative Example 2

According to the procedure described in Example 1 of Japanese unexamined Patent Application Publication No. 2003-305959, 5.0 g of unpurified 2-aminophenol (manufactured by Tokyo Chemical Industry Co., Ltd., purity: 99.5%) and 3.8 g of cinnamoyl chloride were used to synthesize 2.3 g of N-(2-hydroxyphenyl)-cinnamoylamide (yield: 38% in terms of cinnamoyl chloride). The thus obtained crystal was yellow. Melting point: 158-162° C.

Comparative Example 7

According to the procedure described in Example 1 of Japanese unexamined Patent Application Publication No. 2003-305959, 5.0 g of 2-aminophenol, which was obtained by breaking the seal of unpurified 2-aminophenol (manufactured by Tokyo Chemical Industry Co., Ltd., purity: 99.5%) and storing it at room temperature for 1 year, and 3.8 g of cinnamoyl chloride were used to synthesize 8.71 g of N-(2-hydroxyphenyl)-cinnamoylamide (yield: 72.8% in terms of cinnamoyl chloride). The thus obtained crystal was yellow.

Measurement Example 1

Measurement of Whiteness of Powder with Color Difference Meter

The compounds obtained in Examples 1, 2 and 5 and Comparative Examples 1, 2 and 7 were measured for brightness by Hunter and color spaces $L^*$, $a^*$ and $b^*$ by filling a sample of each compound in an accessory cell for powder measurement of a spectrocolorimeter (SD 5000, manufactured by Nippon Denshoku Industries, Co., Ltd.) so as not to transmit light, and measurement was performed under a room temperature atmosphere with a measuring diameter set to 28 mm, and the results are shown in Table 1.

TABLE 1

Results of Measurement of Color Difference (powder)

|  | brightness by Hunter | $L^*$ | $a^*$ | $b^*$ |
|---|---|---|---|---|
| Example 1 | 89.83 | 93.46 | −1.44 | 5.70 |
| Example 2 | 91.20 | 95.11 | −1.27 | 6.08 |
| Example 5 | 85.00 | 89.50 | 0.38 | 7.22 |
| Comparative Example 1 | 84.33 | 94.15 | −4.06 | 13.82 |
| Comparative Example 2 | 73.31 | 84.17 | −0.70 | 20.79 |
| Comparative Example 7 | 69.13 | 85.80 | −2.94 | 30.42 |

It was found from the results shown in Table 1 that the value $b^*$ is high and hence the compound is yellow when 2-aminophenol is used for the production without purification (Comparative Example 1), and that the value $b^*$ is high and hence the compound is yellow also in employing the production process of Japanese unexamined Patent Application Publication No. 2003-305959 (Comparative Example 2). Furthermore, it was found that the value $b^*$ is high and hence the compound is yellow when unpurified 2-aminophenol is used in the production method of the present invention (Comparative Example 7). It was also found that in the case where purified 2-aminophenol is used (Examples 1, 2 and 5), however, the whiteness is excellent and the value $b^*$ is low.

Example 3

Production of Thermal Recording Paper

| Dispersion of color former (Solution A) | |
|---|---|
| 3-di-n-butylamino-6-methyl-7-anilinofluoran | 16 parts |
| 10% polyvinyl alcohol aqueous solution | 84 parts |
| Dispersion of color developer (Solution B) | |
| Compound of Example 1 | 16 parts |
| 10% polyvinyl alcohol aqueous solution | 84 parts |
| Dispersion of filler (Solution C) | |
| calcium carbonate | 27.8 parts |
| 10% polyvinyl alcohol aqueous solution | 26.2 parts |
| water | 71 parts |

("part" denotes parts by mass)

First, mixtures of the aforementioned compositions of the solutions A to C were respectively sufficiently crushed with a sand grinder, so as to prepare dispersion of the components of the solutions A to C, and 1 part by mass of the solution A, 2 parts by mass of the solution B and 4 parts by mass of the solution C were mixed to obtain a coating liquid. The coating liquid was applied on white paper by using a wire rod (manufactured by Webster, Wire bar No. 12) and dried, and the resultant was subjected to a calendering treatment, so as to produce thermal recording paper (in which a dry mass content of the coating liquid was approximately 5.5 g/m$^2$).

Example 6

Thermal paper was produced in the same manner as described in Example 3 except that the compound of Example 1 was replaced with the compound of Example 5 in the dispersion of a color developer (the solution B) of Example 3.

Comparative Example 3

Thermal paper was produced in the same manner as described in Example 3 except that the compound of Example 1 was replaced with 4-hydroxy-4'-isopropoxydiphenylsulfone in the dispersion of a color developer (the solution B) of Example 3.

Comparative Example 4

Thermal paper was produced in the same manner as described in Example 3 except that the compound of Example 1 was replaced with the following compound:

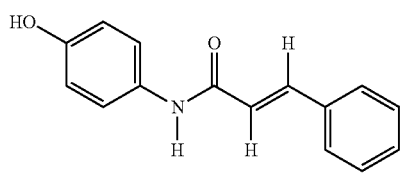 [SMILES: O=C(/C=C/c1ccccc1)Nc1ccc(O)cc1]

in the dispersion of a color developer (the solution B) of Example 3.

Comparative Example 5

Thermal paper was produced in the same manner as described in Example 3 except that the compound of Example 1 was replaced with the following compound:

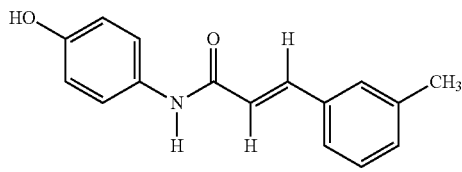 [SMILES: Cc1cccc(/C=C/C(=O)Nc2ccc(O)cc2)c1]

in the dispersion of a color developer (the solution B) of Example 3.

Comparative Example 8

Thermal paper was produced in the same manner as described in Example 3 except that the compound of Example 1 was replaced with the compound of Comparative Example 7 in the dispersion of a color developer (the solution B) of Example 3.

Example 4

Thermal recording paper was produced in the same manner as described in Example 3 except that the white paper of Example 3 was replaced with white paper, which was obtained by applying a dispersion for an undercoat layer having the following composition in a dry mass content of approximately 8 g/m² and drying the resultant:

| Dispersion for undercoat layer | |
|---|---|
| calcium carbonate (manufactured by Shiraishi Kogyo Co., Ltd., Unibur-70) | 27.8 parts |
| 10% polyvinyl alcohol aqueous solution | 26.2 parts |
| water | 71 parts |

Comparative Example 6

Thermal paper was produced in the same manner as described in Example 4 by using the dispersion described in Example 3 except that the compound of Example 1 was replaced with 4-hydroxy-4'-isopropoxydiphenylsulfone in the dispersion of a color developer (the solution B) of Example 3.

Test Example 1

Dynamic Sensitivity

A part of each recording paper produced in Examples and 4 and Comparative Examples 3 to 6 was cut to be subjected to a test for dynamic sensitivity by using a thermal paper color developing sensitivity tester (trade name: TH-PMH, manufactured by Ohkura Electric Co., Ltd.), in which color was developed under a printing voltage of 17 V at pulse widths of 0.2, 0.35, 0.5, 0.65, 0.8, 0.95, 1.1, 1.25, 1.4, 1.6 and 1.8 ms, and the thus attained printing densities were measured by using a Macbeth reflection densitometer (trade name: RD-19I, manufactured by Gretag-Macbeth AG).

The results are shown in FIG. 1 together. In addition, values obtained in color development at pulse widths of 1.1 and 1.25 ms are shown in Table 2 below as representative values. It was understood from these results that the thermal recording paper of Example 3 shows color developing sensitivity equivalent to 4-hydroxy-4'-isopropoxydiphenylsulfone and that an aromatic compound on a side of aminophenol may attain higher dynamic sensitivity when an amino group and a phenol group are substituted in ortho-position instead of para-position.

TABLE 2

| | Dynamic Sensitivity | |
|---|---|---|
| | Pulse Width | |
| | 1.1 ms | 1.25 ms |
| Example 3 | 0.80 | 1.02 |
| Example 4 | 1.20 | 1.30 |
| Comparative Example 3 | 0.93 | 1.14 |
| Comparative Example 4 | 0.42 | 0.62 |
| Comparative Example 5 | 0.43 | 0.60 |
| Comparative Example 6 | 1.13 | 1.30 |

It was found from Table 2 that the thermal recording paper of the present invention has dynamic sensitivity equivalent to that of a commercially available color developer through comparison between Example 3 and Comparative Example 3 and between Example 4 and Comparative Example 6. Furthermore, it was found that the thermal recording paper of the present invention may be further improved in the dynamic sensitivity when a color developing layer is applied after applying an undercoat layer.

Measurement Example 2

Results of Measurement of Color Difference of Thermal Paper

The ISO whiteness of each recording paper produced in Examples 3 and 6 and Comparative Example 8 was measured by using a spectrophotometer (FP 10, manufactured by Nippon Denshoku Industries, Co. Ltd.), and the color spaces L*, a* and b* of the recording paper were measured by using a spectrophotometer (Spectroeye LT, manufactured by X-rite Inc.). The results are shown in Table 3.

TABLE 3

Results of Measurement of Color Difference
(thermal paper)

| | ISO Whiteness | L* | a* | b* |
|---|---|---|---|---|
| Example 3 | 80.24 | 94.56 | −0.45 | 1.39 |
| Example 6 | 65.30 | 92.30 | −1.87 | 9.75 |
| Comparative Example 8 | 59.77 | 91.89 | −3.29 | 14.44 |

As a result of evaluation of color difference performed in the thermal paper actually produced as above (Table 3), it was found that the ISO whiteness and the color spaces a* and b* were poor when unpurified 2-aminophenol was used (Comparative Example 8).

Furthermore, when purified 2-aminophenol is used, in the case where the production method of the present invention (note 1) was employed for the production (Example 3), the ISO whiteness and the color spaces a* and b* are superior as compared with the case where the known production method (note 2) was employed (Example 6).

note 1: The production method of the present invention is a method in which 2-aminophenol and cinnamoyl chloride are used in an equimolar amounts, sodium hydrogencarbonate is used as an alkali compound for the reaction, crystal is separated from a mixed solvent of methanol and water, and the crystal is washed with water.

note 2: The known production method is a method in which 2-aminophenol and cinnamoyl chloride are used in a molar ratio of 2:1 for the reaction, and crystal is separated from a mixed solvent of toluene/methyl isobutyl ketone.

CONCLUSION

In order to produce a color developer excellent in whiteness of a background, it is always necessary to satisfy the first requisite, and in addition, the second requisite and the third requisite are preferably satisfied. According to the production method of the present invention, a cinnamic acid amide-based phenol compound that is free from coloring of its crystal and is also free from coloring when used in producing thermal paper may be obtained for the first time.

INDUSTRIAL APPLICABILITY

According to the present invention, when a specific cinnamic acid amide-based phenol compound is used as a color developer, an unprecedented recording material that is excellent in whiteness of a background, has good color developing performances and has high storage property for both a background and an image, and particularly, a recording material that is excellent in whiteness of a background and is practically extremely excellent in color developing performances may be obtained.

The invention claimed is:

1. A phenol compound represented by Formula (I):

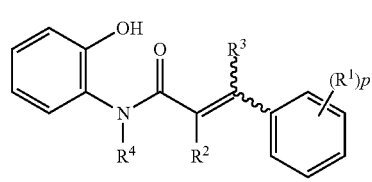

wherein:
R$^1$ represents a hydroxyl group, a halogen atom, a C$_1$-C$_6$ alkyl group, or a C$_1$-C$_6$ alkoxy group,
p represents 0 or an integer of 1 to 5,
R$^2$ and R$^3$ each independently represents a hydrogen atom or a C$_1$-C$_6$ alkyl group,
R$^4$ represents a hydrogen atom, a C$_1$-C$_6$ alkyl group, an optionally substituted phenyl group or an optionally substituted benzyl group;
a bond shown with a wavy line represents cis-trans isomerism, where for each molecule of the compound represented by Formula (I), R$^3$ is independently in a cis or a trans configuration relative to R$^2$; and
the phenol compound has a color space b* of 10 or less.

2. The phenol compound according to claim 1, wherein the phenol compound has brightness by Hunter of 75 or more.

3. The phenol compound according to claim 1, wherein the phenol compound is a compound obtained by a reaction of a purified compound represented by Formula (II):

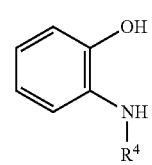

wherein R$^4$ has the same meaning as defined in Formula (I), with a compound represented by Formula (III):

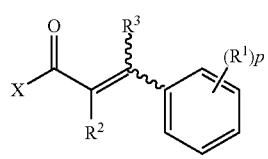

wherein R$^1$ to R$^3$ and p have the same meaning as defined in Formula (I), and X represents a hydroxyl group or a halogen atom, in the presence of a base, followed by crystallization.

4. The phenol compound according to claim 3, wherein the base is a weak alkaline inorganic compound.

5. The phenol compound according to claim 3, wherein the crystallization is conducted by using a polar solvent as a crystallization solvent.

6. A recording material comprising a color former and at least one phenol compound according to claim 1.

7. A recording sheet comprising, on a support, a recording material layer made of a recording material according to claim 6.

* * * * *